14 Claims, 10 Drawing Sheets

(12) United States Patent
Castora et al.

(10) Patent No.: US 7,644,834 B2
(45) Date of Patent: Jan. 12, 2010

(54) SPLASH MINIMIZING LID FOR LIQUID WASTE RECEPTACLE

(75) Inventors: Valarie Castora, Stillwater, NY (US); Kip Moen, Edina, MN (US); Mark Van Diver, Argyle, NY (US); Tim Hall, Ballston Spa, NY (US); Kristina Ernst, Hudson Falls, NY (US); Peter Pendergrass, Salem, NY (US); Dennis C. Deutsch, Queensbury, NY (US)

(73) Assignee: Navilyst Medical, Inc., Marlborough, MA (US)

( * ) Notice: Subject to any disclaimer, the term of this patent is extended or adjusted under 35 U.S.C. 154(b) by 764 days.

(21) Appl. No.: 10/854,879

(22) Filed: May 27, 2004

(65) Prior Publication Data

US 2005/0267425 A1 Dec. 1, 2005

(51) Int. Cl.
*B65D 25/00* (2006.01)
*B65D 51/00* (2006.01)
*B65D 51/18* (2006.01)
(52) U.S. Cl. .................... 220/731; 220/229; 220/370; 220/253
(58) Field of Classification Search .............. 220/229, 220/370, 372, 369, 253, 360, 367.1, 203.28
See application file for complete search history.

(56) References Cited

U.S. PATENT DOCUMENTS

| | | | | |
|---|---|---|---|---|
| 1,020,077 | A * | 3/1912 | Bowser | 220/88.2 |
| 1,256,184 | A * | 2/1918 | Tolman | 220/231 |
| 1,983,139 | A * | 12/1934 | Lovell | 220/256.1 |
| 2,215,607 | A * | 9/1940 | Eastwood | 210/465 |
| 2,751,901 | A * | 6/1956 | Livermore | 126/384.1 |
| 3,899,100 | A * | 8/1975 | Rigaud | 220/229 |
| 4,037,754 | A * | 7/1977 | Wilhelmi et al. | 220/254.2 |
| 4,053,084 | A * | 10/1977 | Anderson | 220/229 |
| 4,091,956 | A * | 5/1978 | Vecchio | 220/231 |
| 4,600,112 | A | 7/1986 | Shillington et al. | |
| 4,816,307 | A | 3/1989 | Honeycutt | |
| 4,913,309 | A | 4/1990 | Fink | |
| 4,921,124 | A * | 5/1990 | Stammler et al. | 220/372 |
| 5,111,946 | A * | 5/1992 | Glanz | 215/247 |
| 5,184,720 | A | 2/1993 | Packer et al. | |

(Continued)

FOREIGN PATENT DOCUMENTS

EP 0 842 641 5/1998

(Continued)

*Primary Examiner*—Anthony Stashick
*Assistant Examiner*—Niki M Eloshway
(74) *Attorney, Agent, or Firm*—Orrick Herrington & Sutcliffe, LLP

(57) ABSTRACT

A liquid medical waste receptacle includes an open top vessel having a bottom and an upstanding wall defining an upper rim. A lid is adapted to cover the open top vessel in sealing engagement with the upper rim. The lid includes a body portion defining a recess portion. The recess portion extends into the open top vessel. In some embodiments, the recess portion makes up a majority of the body portion. In some embodiments, the recess portion has a plurality of fingers. Select fingers have a proximal section, a distal section, and an intermediate section disposed between the proximal and distal sections, wherein the proximal section or the intermediate section includes a flexibility that is greater than the flexibility of at least a portion of the distal section.

U.S. PATENT DOCUMENTS

| | | | | |
|---|---|---|---|---|
| 5,249,696 A * | 10/1993 | Bryant et al. | ............ | 220/367.1 |
| 5,323,902 A | 6/1994 | Palmer et al. | | |
| 5,474,180 A | 12/1995 | Robinson et al. | | |
| 5,483,999 A | 1/1996 | Lampropoulos et al. | | |
| 5,495,941 A | 3/1996 | Leonard | | |
| 5,570,783 A | 11/1996 | Thorne et al. | | |
| 5,630,505 A * | 5/1997 | Garcia | .................... | 206/362.1 |
| 5,630,506 A | 5/1997 | Thorne et al. | | |
| 5,647,502 A | 7/1997 | Marsh | | |
| 5,823,340 A | 10/1998 | Maihofer | | |
| 5,960,837 A | 10/1999 | Cude | | |
| 6,053,314 A | 4/2000 | Pittman | | |
| 6,056,146 A * | 5/2000 | Varakian et al. | ............. | 220/370 |
| 6,095,033 A * | 8/2000 | Melton | ...................... | 99/323.3 |
| 6,112,452 A * | 9/2000 | Campbell | .................... | 43/107 |
| 6,123,188 A | 9/2000 | Ahonen | | |
| 6,152,902 A | 11/2000 | Christian et al. | | |
| 6,585,114 B2 | 7/2003 | Kennedy et al. | | |
| 6,719,017 B1 | 4/2004 | McArthur et al. | | |
| 6,733,481 B2 | 5/2004 | Ow | | |
| 6,889,859 B1 * | 5/2005 | Leon | ........................ | 220/254.3 |
| 7,001,442 B2 * | 2/2006 | Nakatani et al. | ............... | 55/523 |
| 2003/0038133 A1 * | 2/2003 | Liu | ............................ | 220/253 |
| 2004/0245250 A1 * | 12/2004 | Hidalgo et al. | .............. | 220/229 |

FOREIGN PATENT DOCUMENTS

| | | |
|---|---|---|
| EP | 0 875 210 | 11/1998 |
| WO | WO 97/40869 | 11/1997 |
| WO | WO 2004/060178 | 7/2004 |

\* cited by examiner

SPLASH MINIMIZING LID FOR LIQUID WASTE RECEPTACLE

BACKGROUND

The invention relates generally to receptacles for contaminated wastes, particularly splash minimizing receptacles for contaminated liquid medical wastes.

Receptacles for contaminated liquid medical wastes desirably are unobtrusively positioned, yet readily accessible, within the theater of operations for a given medical procedure. One failure of the prior art receptacles for liquid medical wastes relates to the introduction of the liquid waste into the receptacle. In this respect, it is noted that in many medical procedures, there is a degree of urgency to complete the treatment, almost irrespective of the nature of the injury or medical condition being treated. This factor leads to hurried movements, and disposal of liquid medical waste presents one of the more problematic aspects of safety to the medical personnel and/or the patient. More specifically, much of the liquid medical waste generated during a medical procedure is collected or accumulated in a syringe, and in some instances the same syringe is used to collect multiple volumes of liquid from a patient. Emptying the liquid from the syringe between collections is often accomplished quickly. This factor can lead to splatter of liquid being expelled from the syringe, either from the syringe not being properly inserted into a receptacle for the liquid or splatter from the receptacle itself.

A number of different structures and assemblies, and methods of making and using receptacles for contaminated wastes are known, each having certain advantages and disadvantages. However, there is an ongoing need to provide alternative structures, assemblies, and methods for making and using receptacles for contaminated wastes.

SUMMARY OF SOME EMBODIMENTS

The invention generally relates to splash minimizing receptacles for contaminated liquid medical wastes. At least some embodiments are configured to allow a user to use the liquid waste receptacle as if it were an open waste receptacle, i.e., to inject contaminated liquid into the waste receptacle a distance from the receptacle lid or opening, while reducing the risk of spraying and splashing the contaminated fluids onto surrounding instruments, surfaces and/or personnel.

One example embodiment includes a liquid medical waste receptacle including an open top vessel, and a lid adapted to cover the open top vessel. The lid includes a rim and a body portion, and the body portion defines a recess portion adapted to extend into the open top vessel. The recess portion has a plurality of fingers adapted to extend into the open top vessel. At least selected fingers of the recess portion have a proximal section, a distal section, and an intermediate section disposed between the proximal and distal sections, and either the proximal section or the intermediate section, or both, includes a flexibility that is greater than the flexibility of at least a portion of the distal section.

In another example embodiment, the lid comprises a rim and a body portion, and the body portion defines a recess portion extending into the open top vessel, and the recess portion comprises a screen.

In another example embodiment, the recess portion includes a plurality of annular apertures defined therein.

In another example embodiment, the recess portion includes a plurality of apertures and a movable mating portion disposed on the recess portion. The movable mating portion has solid portions and corresponding aperture portions configured to mate with the recess portion plurality of apertures. Selective circumferential movement of the movable mating portion selectively places solid portions of the movable mating portion over the recess portion plurality of apertures.

In another example embodiment, the recess portion includes an opening defined therein, and a plunger is disposed within the opening. The plunger is configured to move between an upper open position and a lower closed position, wherein the plunger in the closed position closes the opening.

In another example embodiment, the recess portion includes a plurality of fingers extending into the open top vessel, wherein selected fingers have a proximal section, a distal section, and an intermediate section. The lid also includes means for increasing the flexibility of the proximal section or intermediate section relative to the flexibility of at least a portion of the distal section of the fingers.

Some other example embodiments are directed to a method of making a liquid medical waste receptacle. An example of such an embodiment includes providing an open top vessel having a bottom and an upstanding wall defining an upper rim, and providing a lid adapted to cover the open top vessel in engagement with the upper rim. The lid includes a rim and a body portion. The body portion defines a recess portion having a plurality of fingers adapted to extend into the open top vessel, wherein at least selected fingers have a proximal section, a distal section, and an intermediate section disposed between the proximal and distal sections. The proximal section or the intermediate section of the selected fingers includes a flexibility that is greater than the flexibility of at least a portion of the distal section. The method further includes disposing the lid on the open top vessel in engagement with the upper rim.

Some other example embodiments are directed to a method of using a liquid medical waste receptacle. An example of such an embodiment includes providing an open top vessel having a bottom and an upstanding wall defining an upper rim and a lid adapted to cover the open top vessel in sealing engagement on the upper rim. The lid includes a body portion defining a recess portion, the recess portion extending into the open top vessel and defining one or more openings into the vessel. The method also includes directing an amount of liquid medical waste toward the recess portion from a liquid medical waste carrier while the carrier is spaced away from the recess portion such that the recess portion directs the liquid medical waste into the vessel through the one or more openings.

Some other example embodiments are directed to a liquid medical waste receptacle lid. In one example embodiment, the lid includes a rim adapted to engage a liquid medical waste open top receptacle, and a body portion adapted to cover at least a portion of the open top vessel. The body portion defines a recess portion adapted to extend into the open top vessel when the lid is disposed on the liquid medical waste open top receptacle. The recess portion includes a plurality of fingers, wherein at least select fingers have a proximal section, a distal section, and an intermediate section disposed between the proximal and distal sections. The proximal section or the intermediate section of the select fingers includes a flexibility that is greater than the flexibility of at least a portion of the distal section.

The above summary of some embodiments is not intended to describe each disclosed embodiment or every implementation of the present invention. The Figures, and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
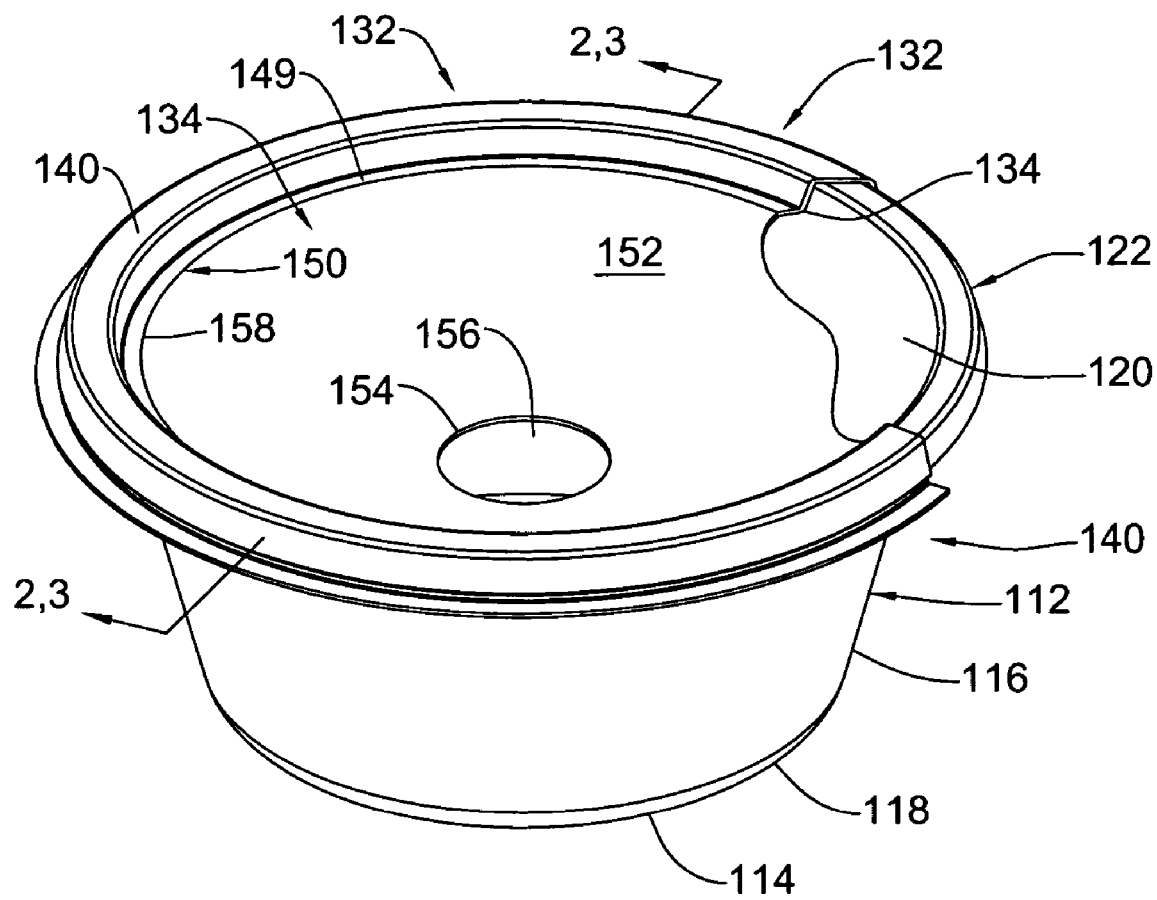
FIG. 1 is a perspective view of an example embodiment of a containment receptacle.

While the invention is amenable to various modifications and alternative forms, specifics thereof have been shown by way of example in the drawings and will be described in detail. It should be understood, however, that the intention is not to limit the invention to the particular illustrative embodiments described. On the contrary, the intention is to cover all modifications, equivalents, and alternatives falling within the spirit and scope of the invention.

DETAILED DESCRIPTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials may be illustrated for the various elements, those skilled in the art will recognize that many of the examples provided have suitable alternatives that may be utilized.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers subsumed within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Some embodiments relate to splash minimizing receptacles for contaminated liquid medical wastes. For example, some embodiments are configured to allow a user to use the liquid waste receptacle as if it were an open waste receptacle, i.e., to inject contaminated liquid into the waste receptacle a distance from the receptacle lid or opening, while minimizing the risk of spraying and splashing the contaminated fluids onto surrounding instruments, surfaces and/or personnel. In some embodiments, the liquid waste receptacle lid includes a body defining a recess portion that forms the majority of the lid. The recess portion can be configured to change a contact angle of a stream of liquid hitting the recess portion, absorb energy from the stream of liquid hitting the recess portion, and/or direct at least a majority of the stream of liquid into the open top vessel through one or more openings in the recess portion. For example, in some embodiments, the shape, size, and/or physical characteristics, for example flexibility, of the recess portion can be adapted to change the contact angle, absorb energy, and/or direct the stream of liquid into the vessel through the one or more openings. In essence, the recess portion can act somewhat like a funnel to change the angle of the fluid, and direct the fluid into the vessel. While the invention is not so limited, an appreciation of various aspects of the invention will be gained through a discussion of the various illustrative embodiments and examples provided below.

Referring to FIG. 1, there is provided a vessel 112 which includes a bottom 114, and a wall 116 formed of unitary construction with, or otherwise joined with, the outer margin 118 of the bottom 114 and upstanding therefrom to define an open top 120 having a rim 122. In the embodiment shown, the vessel 112 is generally circular in shape, wherein the margin 118 and the rim 122 are generally circular in shape. However, in other embodiments, the vessel 112 may be any shape as desired, for example, square, rectangular, oval, elliptical, polygonal, or combinations thereof, or the like. In any case, the outer margin 118 generally defines the periphery of the bottom 114, and the rim 122 generally defines the periphery of the top of the vessel 112. In the depicted embodiment, the wall 116 flares outwardly and upwardly from the bottom 114 so the size of the vessel at its open top is greater than its size adjacent the bottom 114. In other embodiments, the wall 116 may be perpendicular to the bottom 114 such that the top and bottom are generally the same in size, or may flare inwardly such that the size of the vessel 112 at its open top is less than its size adjacent the bottom 114.

Figure 2:
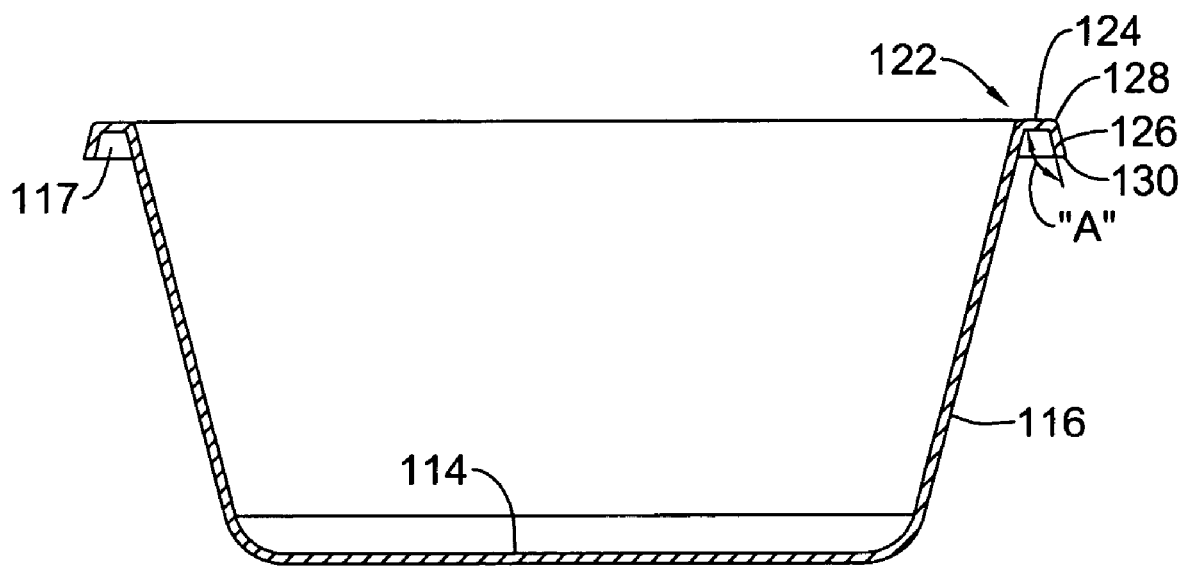
FIG. 2 is a side elevation view, in cross-section, of the receptacle of FIG. 1 taken generally along line 2-2 of FIG. 1.

FIG. 2 is a side elevation view, in cross-section, of the open top vessel of FIG. 1 taken generally along line 2-2 of FIG. 1. The depicted rim 122 includes a lateral flange portion 124 and a lip portion 126 which depends from the outer peripheral edge 128 of the flange portion. The lip portion 126 can define an angle "A" with the flange portion 124. In some embodiments, the angle "A" may be an obtuse angle such that the lower edge 130 of the lip portion projects slightly outwardly from the vessel wall 116. However, in other embodiments, the angle "A" may be a right angle, or may be an acute angle, for example, depending upon the particular mating configuration desired between the vessel 112 and the lid 132. As desired, gussets 117 may be provided between the wall 116 and the circumferential lip portion 126 to rigidify the lip portion 126.

Figure 3:
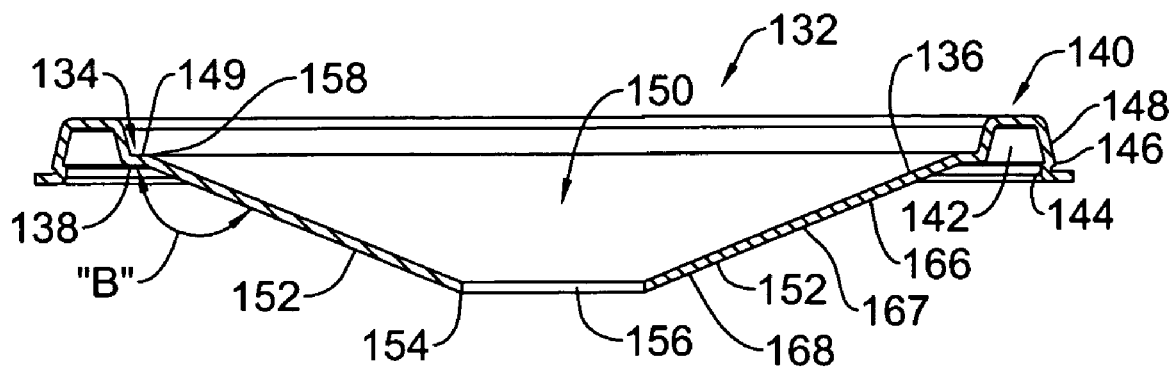
FIG. 3 is a side elevation view, in cross-section, of the lid of FIG. 1 taken generally along line 3-3 of FIG. 1.

FIG. 3 is a side elevation view, in cross-section, of the lid 132 of FIG. 1 taken generally along line 3-3 of FIG. 1. The lid 132 can include an outer or rim portion 140 and a body portion 134 which is bounded by the rim portion 140. The lid 132 can include a top surface 136 and a bottom surface 138. In the embodiment shown, the rim 140 includes a channel 142 that opens downwardly of the lid 132 to receive therein the rim 122 of the vessel 112 in sealing engagement therebetween when the lid 132 is disposed in covering relationship to the open top of the vessel 112. In the depicted embodiment, the rim portion 140 includes a lip 144 disposed on the lower edge 146 of the outermost wall 148 of the channel 142 which is disposed in position to snap over the edge 130 of the vessel 112 to thereby enhance the fluid-tight sealing engagement of the lid 132 with the vessel 112.

The lid 132 and/or the vessel 112 can include any of a broad variety of other and/or alternative structure and/or attachment or sealing configurations between the lid 132 and the vessel 112, as will be understood to those of skill in the art and others. For example, other attachment and/or sealing configurations between the lid 132 and the vessel 112 may include snap, frictional, tongue and groove, threading engagement and/or other mechanical attachment configurations, adhesive bonding, welding, or the like, or even unitary construction of the lid 132 and vessel 112, or the like. Additionally, other structures, such as gaskets, sealing members and/or material, or the like, may also be used to provide sealing between the lid 132 and the vessel 112. In the embodiment shown, the lid 132 is generally circular in shape, wherein the rim 140 and the body 134 are generally circular, for example, to mate with the generally circular vessel 112. However, in other embodiments, the lid 132 may be any shape as desired, for example, to mate with the shape of the open top of the vessel 112. For example, as discussed above, the vessel 112 may be square, rectangular, oval, elliptical, polygonal, or combinations thereof, or the like, and the lid 132 would be appropriately shaped and sized to mate with the vessel 112.

The body portion 134 of the lid 132 includes a recess portion 150 defined therein that is adapted to extend through the open top of the vessel 112 when the lid 132 is mated with the open top of the vessel 112. For example, the wall 152 of the recessed portion 150 may extend through the opening in the top of the vessel 112 such that the wall 152, or at least a portion thereof, is disposed within the vessel 112. The recess 150 may include a top, or proximal portion 166, an intermediate portion 167, and a bottom, or distal portion 168. The bottom portion 168 defines a bottom end 154, which defines an opening 156. The opening 156 allows for fluid communication between the inside of the vessel 112 and the outside of the vessel 112. The opening 156 can be generally defined in and/or by the lowest portion of the recess 150.

In the embodiment shown in FIGS. 1 and 3, the body portion 134 of the lid 132 includes a generally planar portion 149 that is attached to the rim 140, and the recessed portion 150 extends at an angle inwardly and downwardly from the generally planar portion 149. In this embodiment, the outer periphery of the recess portion 150 is defined by the junction 158 between the recess portion 150 and the planar portion 149. The generally planar portion 149 can extend along a horizontal plane that is defined along the base of the rim 140 and that is generally perpendicular to the vertical axis of the lid 132 and/or vessel 112. In other embodiments, the generally planar portion 149 may be absent, and the recessed portion 150 may extend directly from the rim 140. In such embodiments, the outer periphery of the recess portion 150 would be defined by the junction between the rim 140 and the recess portion 150, and the recessed portion 150 would define substantially the entire body portion 134 that is disposed within the rim portion 140. In such embodiments, the recessed portion 150 can extend at an angle inwardly and downwardly from the generally horizontal plane that is defined as extending horizontally from the base of the rim 140 and that is generally perpendicular to the vertical axis of the vessel 112 and/or lid 132.

The wall 152 of the recess 150, when viewed in cross section as in FIG. 3, can define an angle "B" relative to the planar portion 149. In some other embodiments, where the planar portion 149 is absent and the recess portion 150 extends directly from the rim 140, the wall 152 of the recess 150 can define the angle "B" relative to the generally horizontal plane that is defined as extending horizontally from the base of the rim 140 and that is generally perpendicular to the vertical axis of the vessel 112 and/or lid 132. In some embodiments, the angle B may be an obtuse angle, and in some embodiments, may be an obtuse angle in the range of about 100 to about 180 degrees. In other example embodiments, the angle B may be a right angle, or in still other embodiments, may be an acute angle.

The recessed portion 150 can be defined by any of a broad variety of shapes. For example, in the embodiment shown in FIGS. 1 and 3, the recessed portion is generally frustroconical (i.e. a cut off cone) in cross-sectional geometry. In other embodiments, the recess portion 150 may include other cross sectional shapes and/or geometries, for example, a partial sphere (bowl shaped), a pyramid or partial pyramid shape, a cylinder, an hour glass shape, or any of a broad variety of polygonal and/or irregular cross sectional shapes, or the like. In some embodiments, it is generally desired that the recess have a shape which generally has a funneling effect to transmit fluids from the recess 150 into the opening 156. In some embodiments, the shape of the recess portion 150 is generally symmetrical, however, in other embodiments, the shape of the recess portion 150 can be non-symmetrically shaped, as desired.

Likewise, the opening 156 may be defined by any of a broad variety of shapes. The embodiment shown in FIGS. 1 and 3 shows an opening 156 that is generally circular in shape, but other shapes may be suitable, for example, oval, triangular, square, rectangular, oblong, polygonal, or any of a broad variety of other shapes, or the like. The shape of the opening 156 may also be generally symmetrical or non-symmetrical, as desired.

The recess portion 150 and/or the opening 156, or both, may be generally centered within the periphery of the lid 132 as defined by the rim 140, or may be eccentrically positioned within the periphery of the lid 132 relative to the rim 140. In other words, the recess portion 150 and/or the opening 156 may centered or offset from the geometric center of the lid 132.

In many embodiments, the recessed portion 150 takes up the majority of the body 134 of the lid 132. For example, the body portion 134 of the lid 132, which is bounded by the rim portion 140, can define a certain amount of surface area along the upper surface 158 of the lid 132. The majority of the surface area defined by the body is taken up by the recess portion 150. In other words, in embodiments having a body portion 134 including a planar portion 149 and a recess portion 150, the recess portion is bigger and/or takes up more of the body portion 134 than the planar portion 149. For example, in some embodiments, the recess portion 150 can be 60%, 70%, 80%, 90%, 95% or more of the body portion 134. In embodiments that are substantially without a planar portion 149, the recess portion 150 may make up the entire body portion.

The recess portion 150 may also include certain flexibility characteristics that may provide desirable results. For example, the wall 152 of the recessed portion 150 may be provided with flexibility characteristics along the length thereof, as it extends into the vessel 112, that provide for enhanced ability to redirect the flow of a liquid stream into the vessel 112, and minimize splashing. Such flexibility characteristics along the length of the recessed portion 150 as it extends into the vessel 112 may occur in a gradual or tapered manner, or in a stepwise manner, and may be constant or variable. In at least some embodiments, the structure defining the recess portion 150 can include greater flexibility than other portions of the lid 132. Additionally, the flexibility characteristics of the proximal 166, intermediate 167, and the distal 168 portions may be different from one another to provide desirable characteristics. In some embodiments, the intermediate portion 167 and/or the proximal portion 166 may be provided with the more flexibility relative to one or both of the other two portions to provide a region of bending which may help to direct fluid into the vessel 112. In other embodiments, the flexibility characteristics may taper from the distal portion being the most flexible, to the proximal portion being the least flexible, or vice-versa. In yet other embodiments, each or all of the portions 166, 167, and 168 may be provided with flexibility that is greater than the remainder of the lid 132. Any of a broad variety of flexibility configurations can be contemplated, and many structures and/or configurations may be used to achieve the desired flexibility characteristics. For example, the use of notches, grooves, apertures, channels, recesses, areas of reduced material thickness and/or width, or other mechanical and/or geometric structures may be used to achieve desired flexibility characteristics. Additionally, the use of different materials having varying flexibility characteristics along different portions of the recess 150 can be use to achieve desired characteristics. Some example embodiments including particular flexibility characteristics are discussed in more detail below.

The recess portion 150, due to its generally recessed configuration, may change a contact angle of a stream of liquid hitting the recess portion 150, may absorb energy from the stream of liquid hitting the recess portion 150, and/or may direct at least a majority of the stream of liquid into the open top vessel 112 through the opening 156. As discussed briefly above, the flexibility characteristics of all and/or portions of the recessed portion 150 may also aid in these functions. In essence, the recess portion 150 may act somewhat like a funnel to change the angle of the fluid, and direct the fluid into the vessel 112.

This may allow a user to quickly and easily direct a fluid stream into the vessel 112 while the fluid source is a distance away from the vessel. The energy absorption, and thus reduction of the speed at which the fluid contacts the interior of the vessel, and/or the change in the angle of the fluid such that it is directed into the vessel may help to minimize splash and/or splash-back of fluid being directed into the vessel 112.

For example, these features of the recessed portion 150 of the lid 132 may be beneficial when a carrier, for example, a syringe, is used to direct liquid medical waste into the vessel 112. In this situation, the medical technician (e.g., doctor or nurse) desires to empty the liquid contents of a syringe, either for the reason that they need to reuse the syringe to collect further liquid, or they need to dispose of the contents of the syringe so as to minimize the time span when their attention is diverted to the task of disposing of the liquid waste and away from the task of treating the patient. A syringe can in some cases generate a 1 to 3 mm stream of liquid at a pressure of 30 to 75 psi, for example. Under these circumstances, the lid provides for use of the container as if it was open, allowing the user to inject contaminated liquid from the carrier while the carrier is spaced away from the recess portion. The carrier can be spaced away from the recess portion a distance, for example, up to or at least 1 inch, 2 inches, three inches, or 4 inches, while minimizing splatter and splash-back. The lid also does not exhibit sufficient open area for the splatter of the contaminated liquid from the vessel during the course of the expulsion of liquid, under pressure, from the syringe.

It should be understood by those of skill in the art and others that the particular size, shape, and arrangement of the vessel 112 and the lid 132 may include a wide variety of configurations. Therefore, it will be understood that the following examples of particular configurations, as well as the configurations set fourth above, are merely for illustrative purposes, and that a broad variety of other configurations may be used. In some particular embodiments, the vessel 112 may have a capacity in the range of about 50 to about 2000 ml. The lid 132 can be adapted to fit over the open top of the vessel 112, and can include a size (e.g. diameter and/or width) defined by the rim 140 in the range of about 3 to about 30 cm. The recess portion 150 defined in the body 134 of the lid 132 may have a size (e.g. diameter and/or width) in the range of about 2 to about 25 cm. The opening 156 defined in the recess portion 150 may have a size (e.g. diameter and/or width) in the range of about 0.5 to about 20 cm, or less. In some embodiments, the size of the recess 150 can be in the range of about 1 to 10 times that of the size of the opening 156. In some embodiments, the size of the recess portion 150 can be in the range of about 0.3 to 1.0 times of the size of the lid 132 (defined by the rim portion 140). The height of the recess 150, which is defined as the distance between the opening 156 and the generally horizontal plane that is defined as extending horizontally from the base of the rim 140 that is generally perpendicular to the vertical axis of the vessel 112 and/or lid 132, can be generally in the range of about 0.5 to about 10 cm, or less. In any regard, the construction of the recess 150 can be adapted and chosen for the purpose of reducing the likelihood of splatter of liquid from the interior of the vessel 112 out through the opening 156, during the course of addition of liquid waste into the vessel 112 or when handling the vessel after it has been partially or fully filled with liquid waste.

It should also be noted that in some embodiments, the components of the lid 132, for example the rim portion 140, the body portion 134, including the recess portion 150 and the planar portion 149 (if any) can be of unitary construction. For example, in such embodiments, the lid 132 may be formed using a manufacturing technique such that the entire lid 132 is one unitary piece defining the different structures therein. In other embodiments, however, two or more of the components of the lid 132 may be made separately, and thereafter constructed or put together, either permanently, or selectively removably from one another, to form the finished lid 132. For example, the rim portion 140 and the planar portion 149 (if any) may be made separately from the recessed portion 150. Thereafter, the recessed portion 150 may be inserted into or otherwise permanently or removably combined with the rim portion 140 and the planar portion 149 (if any) to create the lid 132. This is true for any of the embodiments disclosed herein.

Figure 3A:
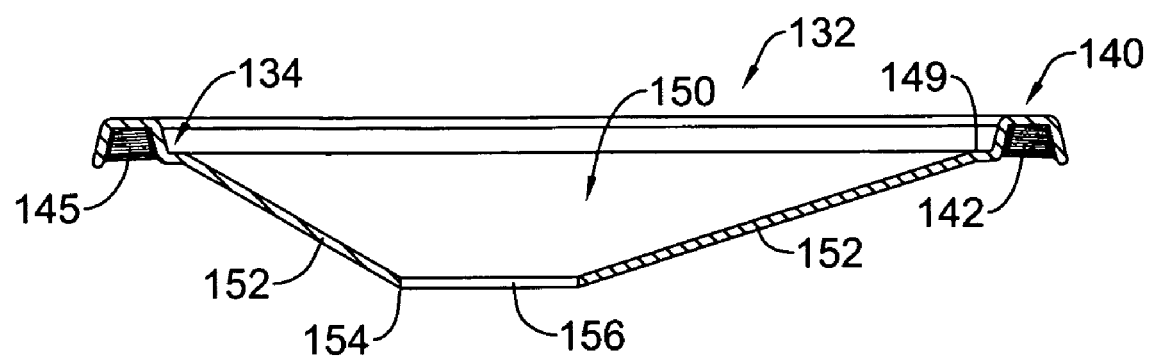
FIG. 3A and FIG. 3B are side elevation views, in cross-section, of alternate lid embodiments of FIG. 3.
Figure 3B:
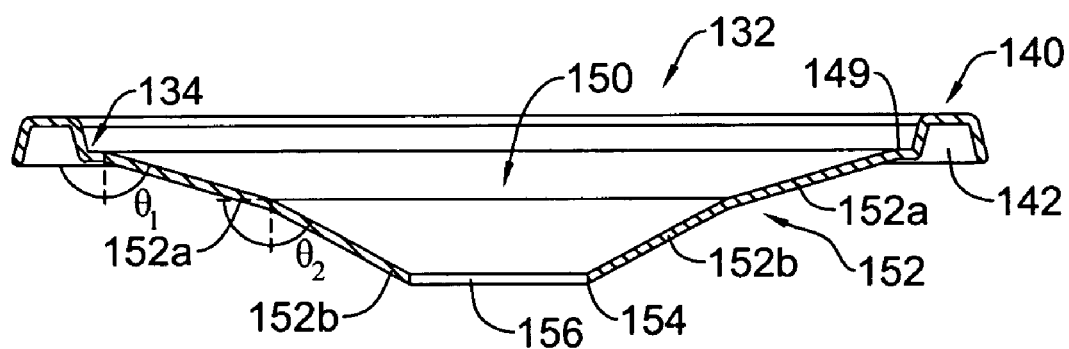

FIG. 3A and FIG. 3B are side elevation views, in cross-section, of alternate lid embodiments similar to that shown in FIG. 3, wherein similar reference numbers indicate generally similar structure. FIG. 3A illustrates a lid 132 having an opening 156 that is not generally centrally located within the rim 140. As can be seen in the drawing, the opening 156 is disposed generally closer to one side of the lid 132. Furthermore, the recessed portion 150 is generally non-symmetrical in shape. As can be seen, while the recessed portion 150 is still generally frustroconical in shape, the wall 152 along one side of the recessed portion 150 is significantly longer than the wall 152 along another side of the recessed portion 152, thereby making the angle on one side more aggressive than on the other side.

Furthermore, the lid 132 in this embodiment includes structure than can allow for threaded connection between the lid 132 and a vessel including a threaded upper portion (not shown). The lid 132 can include a body portion 134 bounded by a circumferential rim portion 140. This rim 140 includes a circumferential channel 142 that opens downwardly of the lid to receive therein the rim of the vessel in sealing engagement therebetween when the lid 132 is disposed in covering relationship to the open top of the vessel. The circumferential channel 142 can include threads 145 for sealing engagement with a corresponding threaded open top vessel (not shown).

FIG. 3B illustrates a lid 132 having a recess 150 wherein the wall 152 of the recessed portion 150 includes a plurality of sections 152a, 152b that are set at different angles relative to the planar portion 149 and/or relative to one another. A first recess section 152a can extend at a first angle $\theta_1$ toward the opening 156. A second recess section 152b can extend at a second angle $\theta_2$ toward the opening 156 where the second angle $\theta_2$ is different than the first angle $\theta_1$. The second angle $\theta_2$ can be greater or less than the first angle $\theta_1$, as desired. The recess 150 in other embodiments can include more or fewer such sections (e.g., 152a, 152b) that extend at different angles relative to one another. As discussed above, the recess portion 150 can be any desired shape, but in the particular embodiment shown, is generally frustroconical in cross-sectional geometry. The bottom end 154 of the recess 150 can define the opening 156. It should also be noted that such embodiments may not include the planar portion 149, and the first recess section 152a can extend directly from the rim 140. In such cases the angles $\theta_1$ and $\theta_2$ can be determined relative to the generally horizontal plane that is defined as extending horizontally from the base of the rim 140 and that is generally perpendicular to the vertical axis of the vessel 112 and/or lid 132.

Figure 4:
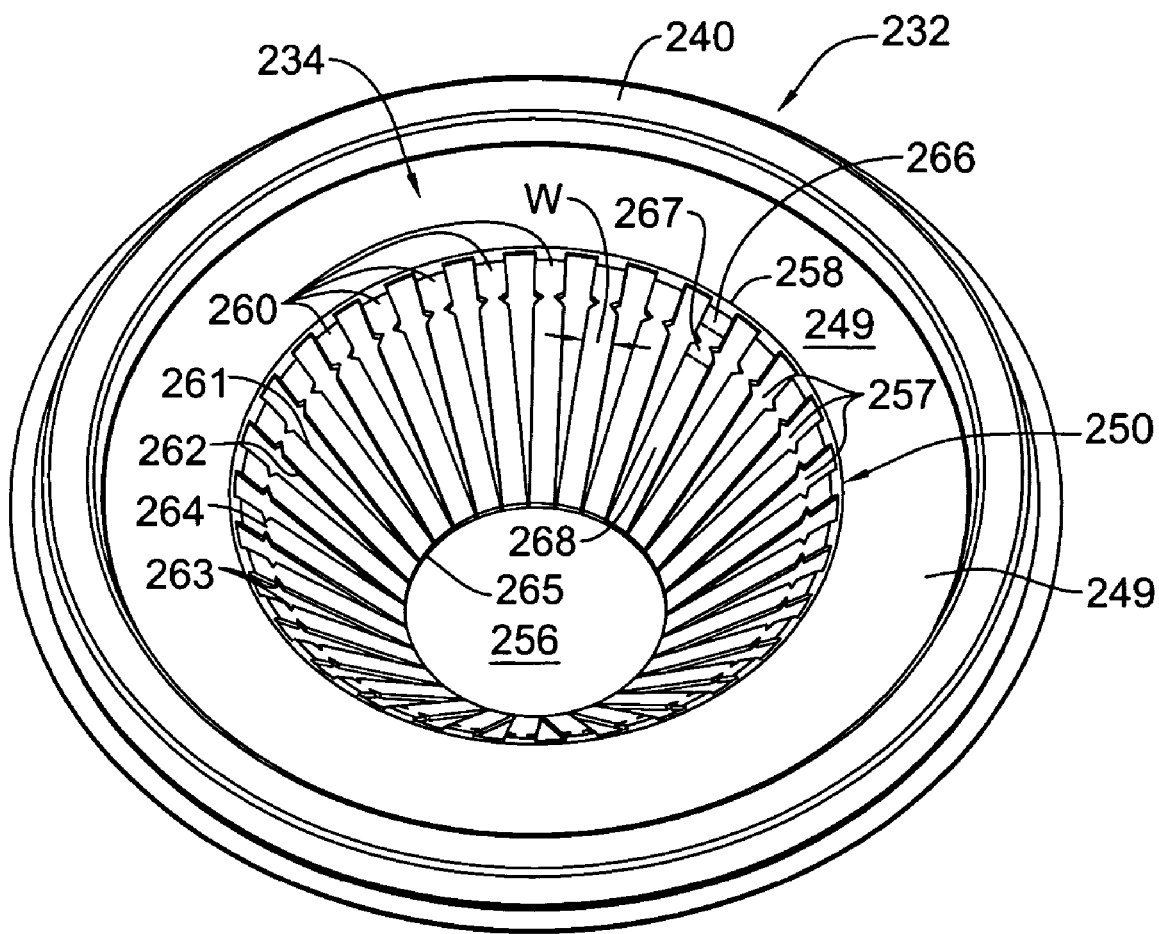
FIG. 4 through FIG. 8 illustrates a variety of example lid embodiments.

FIG. 4 through FIG. 8 illustrates a variety of alternative lid embodiments. FIG. 4 illustrates a lid 232 having a rim portion 240 and a body portion 234. The body portion 234 defines a generally planar portion 249, for example, similar to the planar portion 149 as discussed in the embodiments above, and a recess portion 250 formed by a plurality of fingers 260 extending at an angle generally downwardly and inwardly from a generally planar portion 249. The recess portion 250, defined by the fingers 260, may have many of the same size, shape, and/or other characteristics as the recess portion 150 discussed in the above embodiments. As discussed above, in some embodiments, the generally planar portion 249 may be absent, in which case, the fingers 260 (defining the recessed portion 250) may extend directly from the rim 240. In such embodiments, the outer periphery of the recess portion 250 would be defined by the junction between the rim 240 and the fingers 260, and the recessed portion 250 would define substantially the entire body portion 234.

Each finger 260 can include a proximal section 266, an intermediate section 267, and a distal section 268, defining a distal end 265. In some embodiments, the distal ends 265 of the fingers 260 may be interconnected, but in many embodiments, increased flexibility of the fingers 260 may be desired, so the distal ends 265 are not interconnected. The length of each finger 260 is the distance along the particular finger 260 between the point where the proximal section 266 is connected planar portion 149 (or to the rim 240 in embodiments without a planar portion 249) to the opposing finger distal end 265. The plurality of fingers 260 can be shaped and/or sized to give desired characteristics.

In this embodiment, the fingers 260 are generally longitudinally extending members that are rectangular in cross sectional shape, and have a generally constant width W (other than the notches 263 defined in the intermediate portion 267, as will be discussed below) defined by a distance between a first finger side 261 and a second finger side 262. The fingers 260 in this embodiment also may have a generally constant thickness, while in other embodiments the thickness may vary, for example, to achieve desired flexibility characteristics. In this embodiment, at least a portion of the first finger side 261 is parallel to the second finger side 262. It should be understood, however, that a broad variety of finger sizes, shapes, and configurations may be used. For example, the fingers 260 may include widths and/or thickness that are tapered or otherwise variable along the length of the fingers 260. Additionally, the fingers 260 may have a broad variety of shapes, for example cross sectional, lengthwise and/or thickness shapes. For example, in some embodiments, the fingers 260 may have a round, oval, triangular, square, or other polygonal shape and/or cross-section, or the like.

The fingers 260 can be designed to change a contact angle of a stream of liquid hitting the fingers 260, absorb energy from the stream of liquid hitting the fingers 260, and/or direct at least a majority and up to all of the stream of liquid into the vessel. The illustrative embodiment includes 30 fingers 260 and 30 openings 257 defined by a distance between the fingers 260. The opening 257 can be interconnected and still be defined as a plurality of openings. In some embodiments there are at least 5, 10, 20, 30, 40, 50 or more fingers 260 and/or opening 257. In other embodiments there are 10 to 100 fingers, 20 to 50 fingers, or 25 to 40 fingers, as desired.

As discussed in the embodiments above, sections of the recess portion 250 may include areas of varying flexibility characteristics. The embodiment in FIG. 4 illustrates one such embodiment. As an initial matter, it should be noted that due to the fact that the recess portion 250 is defined by the fingers 260 separated by openings 257, the recess portion 250 may have increased flexibility as a whole relative to other portions of the lid 232. Additionally, in this embodiment, at least a selected plurality of fingers 260 can have a selected area of increased flexibility 264 relative to other areas located along the finger length. In this embodiment, the area of increased flexibility 264 can be located in the intermediate portion 267 along the finger length, between a distal portion 266 and the proximal portion 268. In this embodiment, the area of increased flexibility 264 is achieved by providing at least a part of the intermediate section 267 with an area of reduced width by forming one or more notches 263 in the sides 261/262 of the finger 260. In the embodiment shown, two notches 263 are use, but in other embodiments, more or fewer notches may be used. Due to the area of reduced width defined by the notches 263, the intermediate portion 267 may be more flexible than the distal portion 268, the proximal portion 266, or both. In some embodiments, the intermediate portion 267 may have a flexibility that is at least 1.5, 2, 3, 4, 5, or more times greater than the proximal portion 266, the distal portion 268, or both.

In other embodiments, the one or more areas of increased flexibility may be disposed at other points along the length of the finger 260. For example, an area of increased flexibility may be provided in the proximal section 267 where it attaches to the planar portion 249 and/or to the rim 240. In yet other embodiments, the distal section 268 may be provided with an area of increased flexibility relative to the other sections. Or a plurality of areas or sections having increased flexibility relative to other areas or sections may be incorporated into the fingers 260. For example, the flexibility along the finger 260 may generally increase in the distal direction, such that as you move distally from the proximal section 266, the fingers become more flexible, or vice-versa. Such a transition in flexibility may be gradually tapered, or may occur in a stepwise fashion.

It should also be understood that providing increased flexibility to certain sections of the fingers 260 can be achieved in a broad variety of ways. For example, the thickness of a portion of a finger 260 may be varied, or different structures, such as grooves, apertures, channels, recesses, areas of reduced material thickness and/or width, or other mechanical and/or geometric structures may be used to achieve desired flexibility characteristics. Additionally, the use of different materials or composite materials having varying flexibility characteristics along different portions of the finger 260 can be use to achieve desired characteristics.

The areas of increased flexibility may provide for enhanced ability to redirect the flow of a liquid stream into the vessel 112, and minimize splashing. For example, the intermediate section 267 of FIG. 4 can provide a region of bending which may help to direct fluid into the vessel 112. As a fluid stream hits the finger 260 at or below the intermediate portion 267, the finger 260 may bend at the intermediate section, thereby providing for energy absorption and/or redirecting of the fluid stream into the vessel. The fingers 260 may also act as barriers to prevent splash back from exiting the vessel.

It should be understood that the fingers 260 can be sized and shaped to provide the necessary function as desired, and that the above description and the following particular size ranges are given by way of illustration only. In some example embodiments, the fingers 260 can have a length in the range of about 2 to about 25 cm and a width W in the range of about 1 mm to 5 cm. The selected area of increased flexibility 264 can have a width in the range of about 0.1 mm to about 4 cm.

Figure 5:
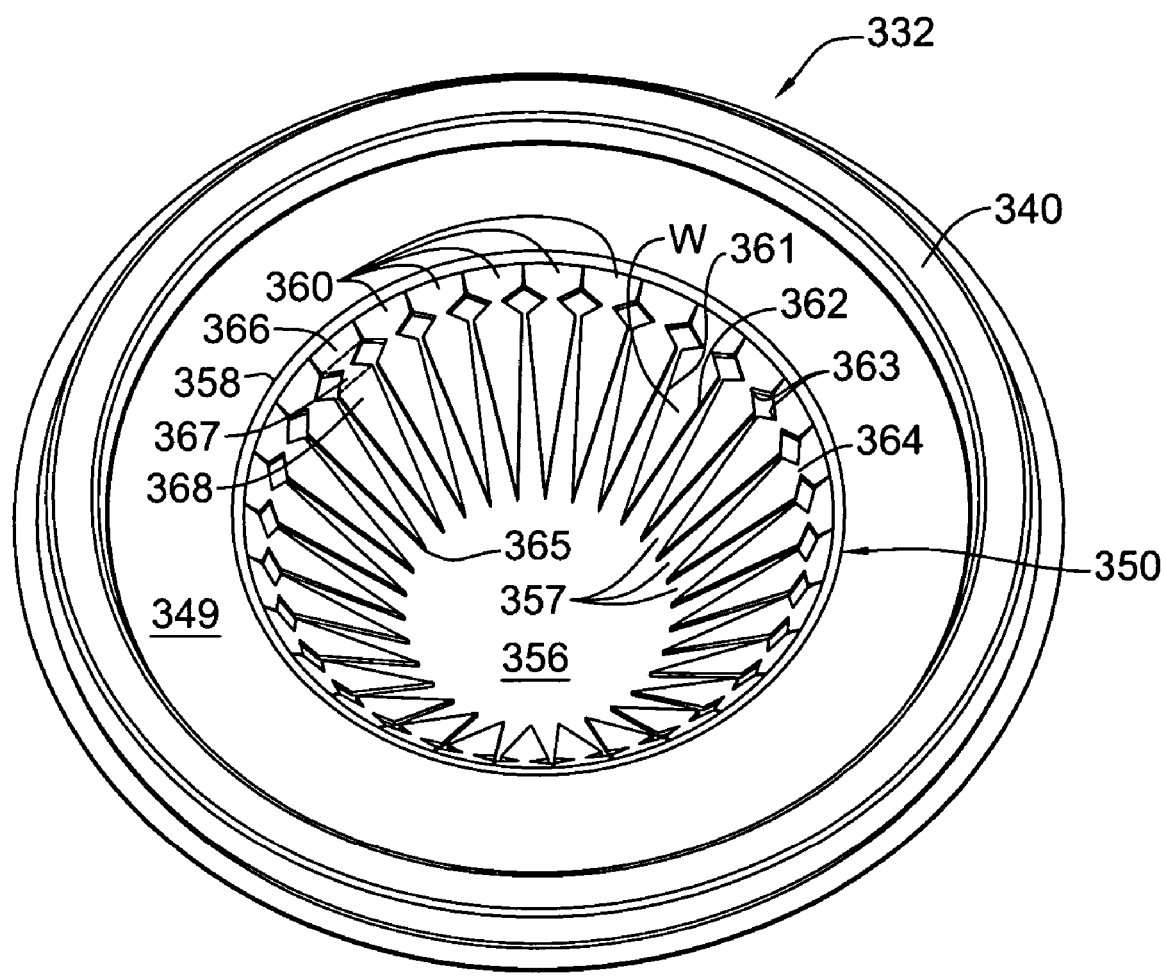

FIG. 5 also illustrates a lid 332 having a body portion 334 including a recess portion 350 formed by a plurality of fingers 360 extending from the planar portion 349 generally inwardly and downwardly toward the opening 356. As discussed above, some embodiments may not include the planar portion 349, in which case the fingers 360 may extend directly from the rim portion 340. In this embodiment, however, the fingers 360 have a generally tapered width W (defined by a distance between a first finger side 361 and a second finger side 362) along the length thereof, such that the proximal portion 366 is the widest, tapering to the distal portion 368, and ultimately the distal end 365, which has the narrowest width. As such, at least a portion of the first finger side 361 is non-parallel to the second finger side 362. The fingers 360 are shown tapering to a pointed end 365, however the end 365 may be blunt. Tapering can aid in increasing the flexibility of at least selected fingers along the finger length.

Again, in this embodiment, at least selected fingers 360 can have an area and/or point of increased flexibility 364 along each finger 360 length. Similar to the embodiment of FIG. 4, the selected area of increased flexibility 364 is illustrated as an area of reduced width formed as one or more notches 363 in the first and second finger sides 361, 362 within the intermediate portion 367 of the finger. However, as discussed above, the selected area of increased flexibility 364 can be formed in any of a broad variety of manners, and may be dispose in one or more other sections along the length of the finger 360, as desired. The recess portion 350, defined by the fingers 360, may have many of the same size, shape, and/or other characteristics as the recess portion 150 discussed in the above embodiments.

As discussed above, the fingers 360 can be designed to change a contact angle of a stream of liquid hitting the fingers 360, absorb energy from the stream of liquid hitting the fingers 360, and direct at least a majority and up to all of the stream of liquid into the vessel. The illustrative embodiment includes 30 fingers 360 and 30 openings 357 defined by a distance between the fingers 360. The opening 357 can be interconnected and still be defined as a plurality of openings. In some embodiments there are at least in the range of 5, 10, 20, 30, 40, 50, or more fingers 360 and/or opening 357. In other embodiments there are in the range of 10 to 100 fingers, 20 to 50 fingers, or 25 to 40 fingers, as desired.

Figure 6:
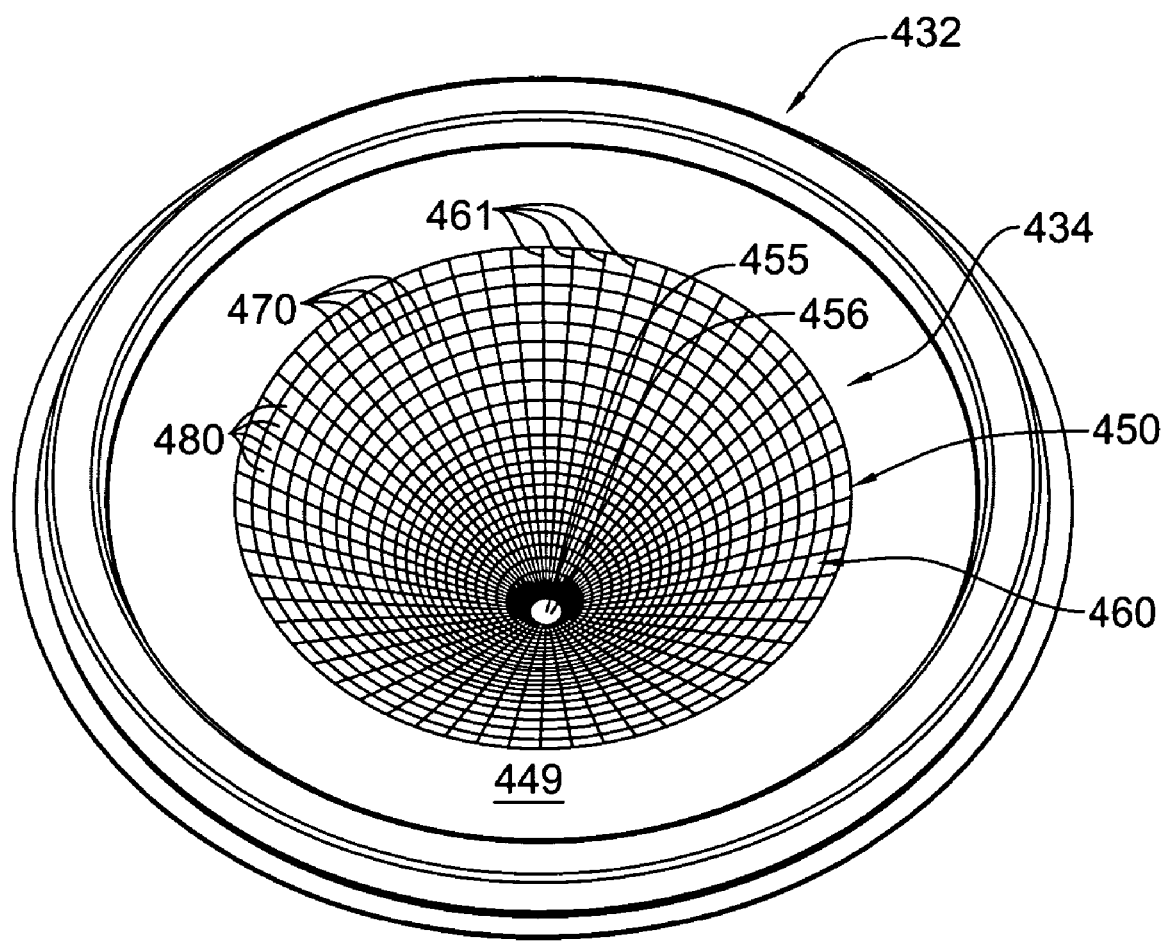

FIG. 6 illustrates a lid 432 having a body portion 434 including a recess portion 450 formed by a screen 460 extending from the planar portion 449 generally inwardly and downwardly toward a recess center 455, which may or may not define an opening 456. As discussed above, some embodiments may not include the planar portion 449, in which case the screen 460 may extend directly from the rim portion 440. The screen 460 can be formed of any useful material such as, for example, metal, polymer, fabric, and the like. The screen can include a plurality of longitudinal elements 470 intersecting a plurality of axial elements 461 forming a plurality of screen openings 480. The screen elements 461, 470 are designed to change a contact angle of a stream of liquid hitting the screen elements 461, 470, absorb energy from the stream of liquid hitting the screen elements 461, 470, and/or direct at least a majority and up to all of the stream of liquid into the vessel through the screen openings 480 and/or opening 456. The illustrative embodiment includes screen openings 480 having an area in the range of 0.1 mm$^2$ to 10 mm$^2$, or from 0.5 mm$^2$ to 5 mm$^2$, however, other sizes may be used, as desired. The screen openings 480 can be uniform in area or increase or decrease in area as a function of position along the screen. For example, the openings 480 can increase or decrease in area the closer they are to the screen center 455. The recess portion 450, defined by the screen 460, may have many of the same size, shape, and/or other characteristics as the recess portion 150 discussed in the above embodiments.

Figure 7:
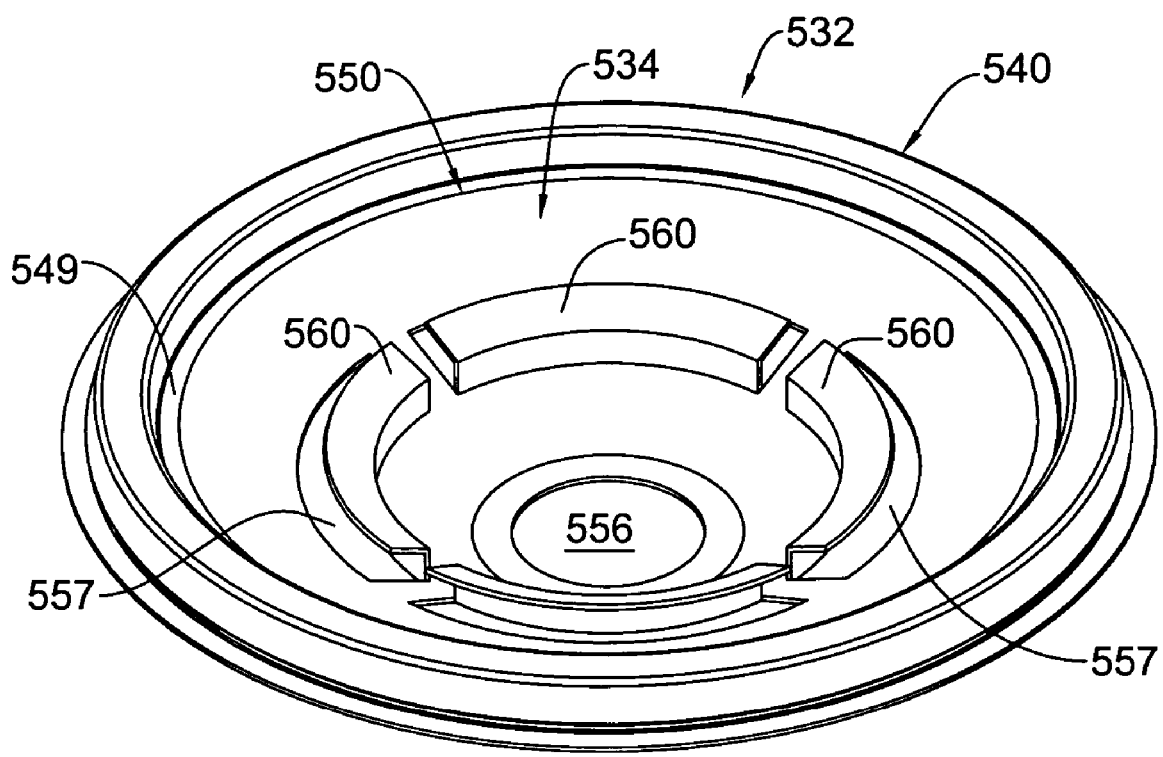

FIG. 7 illustrates a lid 532 having a recess portion 550 that includes a plurality of apertures 557 and/or openings 557 defined within the recess portion 550. In this illustrative embodiment, the lid body portion 534 includes recess portion 550 that extends from the planar portion 549 generally downwardly and inwardly toward the opening 556. As discussed above, some embodiments may not include the planar portion 549, in which case the recess portion 550 may extend directly from the rim portion 540. The annular apertures 557 include an overhang element 560 that extends a distance from the annular aperture 557 and over at least a portion of the annular aperture 557. The overhang element 560 is shown having an "L" shape in cross-section, however the overhang element 560 can have any useful shape such as, for example a "J" shape, a "C" shape, and the like. The annular apertures 557 are shown forming a portion of a common circle around the recess portion 550, however, annular apertures 557 can be placed in any useful manner on the recess portion 550. The overhang element 560 can function to direct a spray of liquid into the vessel and deflect any splash-back back into the vessel, as desired. Four annular apertures 557 are shown in the recess portion 550, however any useful number of annular apertures 557 can be present such as, for example, 2, 3, 4, 5, 6, 7, 8, 9, 10, or more. The recess portion 550, other than including the annular apertures, may have many of the same size, shape, and/or other characteristics as the recess portion 150 discussed in the above embodiments.

Figure 8:
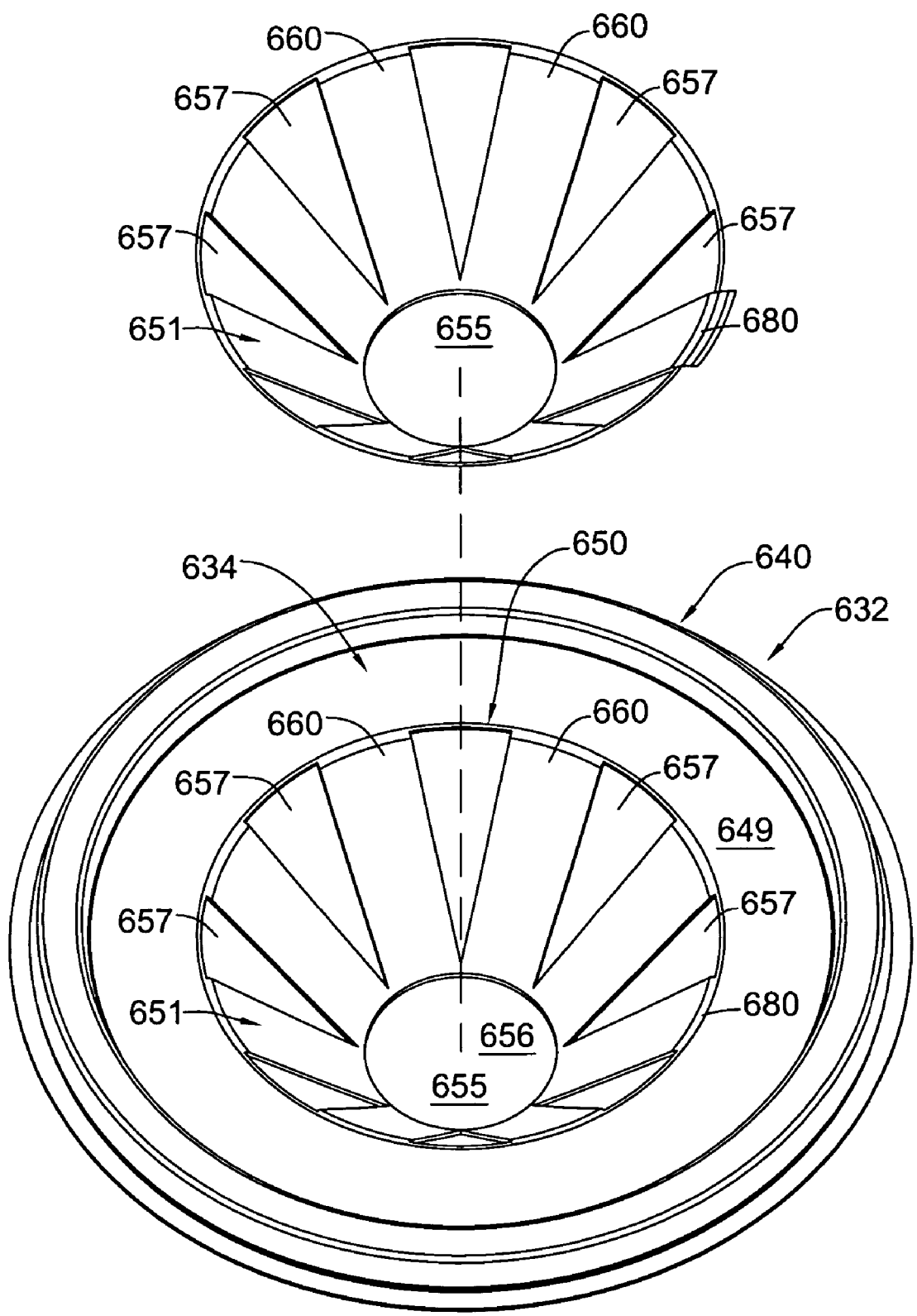

FIG. 8 illustrates an exploded view of a lid 632 having a recess portion 650 that includes a plurality of apertures 657 and/or openings 657. In this illustrative embodiment, the body 634 includes a recess portion 650 that extends from the planar portion 649 generally inwardly and downwardly toward the recess center 655. As discussed above, some embodiments may not include the planar portion 649, in which case the recess portion 650 may extend directly from the rim portion 640. A movable mating portion 651 adapted to mate with and be selectively movable and/or rotatable relative to the recess portion 650 can be disposed on the recess portion 650. The movable mating portion 651 is shown having solid portions 660 and aperture portions 657 configured to mate with the recess portion apertures 657. The movable mating portion 651 can include a handle 680 to aid in moving the movable mating portion 651. Force can be applied to the movable mating portion 651 to cause circumferential and/or rotational movement, about the recess center 655, of the movable mating portion 651 such that solid portions 660 of the movable mating portion 651 to selectively seal and selectively open at least selected apertures 657. Apertures 657 are shown as a pie shape, however apertures 657 can be any useful shape. Recess center 655 can be solid or another opening 656 may be formed as desired. The recess portion 650 may have many of the same size, shape, and/or other characteristics as the recess portion 150 discussed in the above embodiments.

Figure 9:
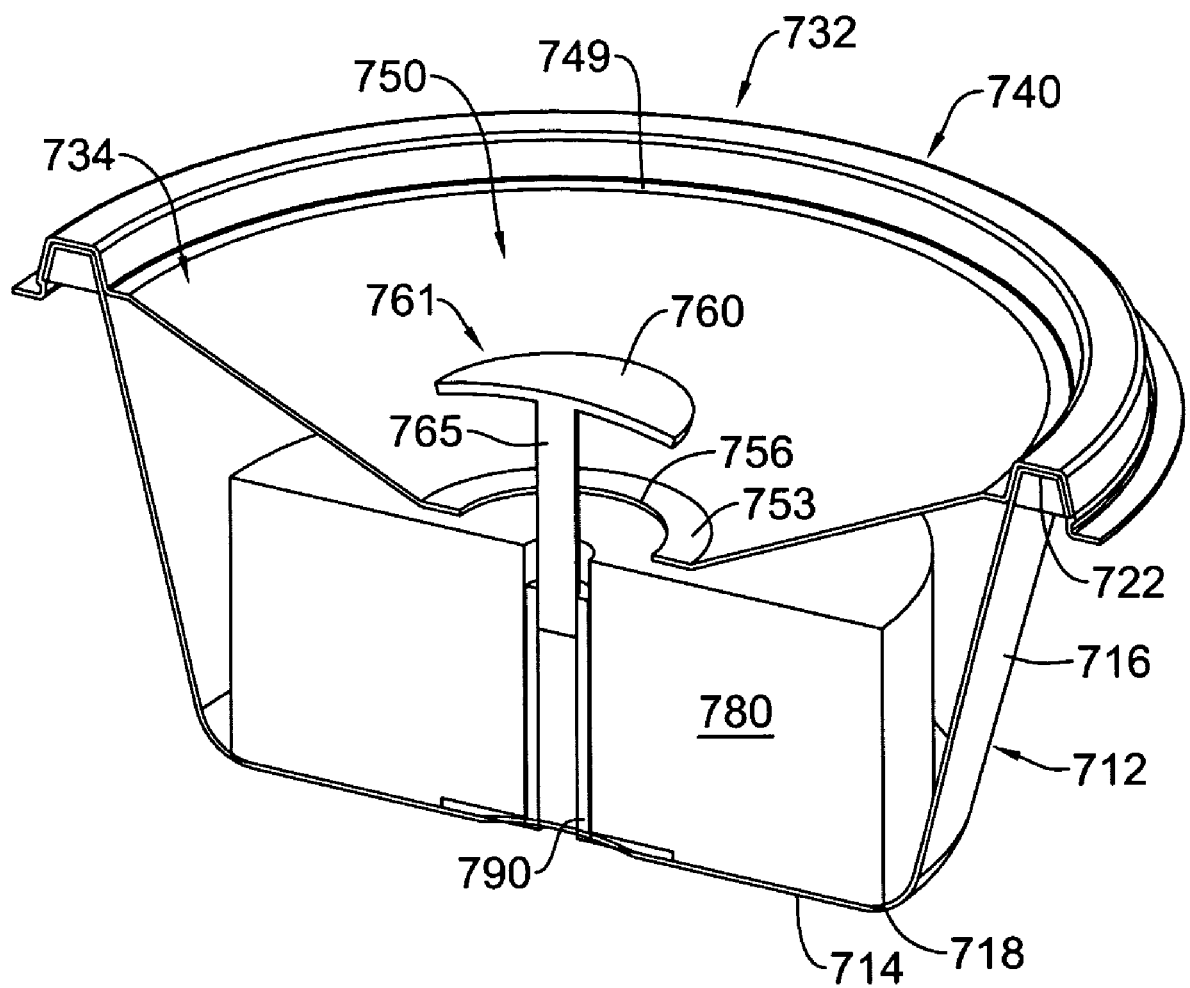
FIG. 9 and FIG. 10 are perspective cross-sectional views of another example containment receptacle.
Figure 10:
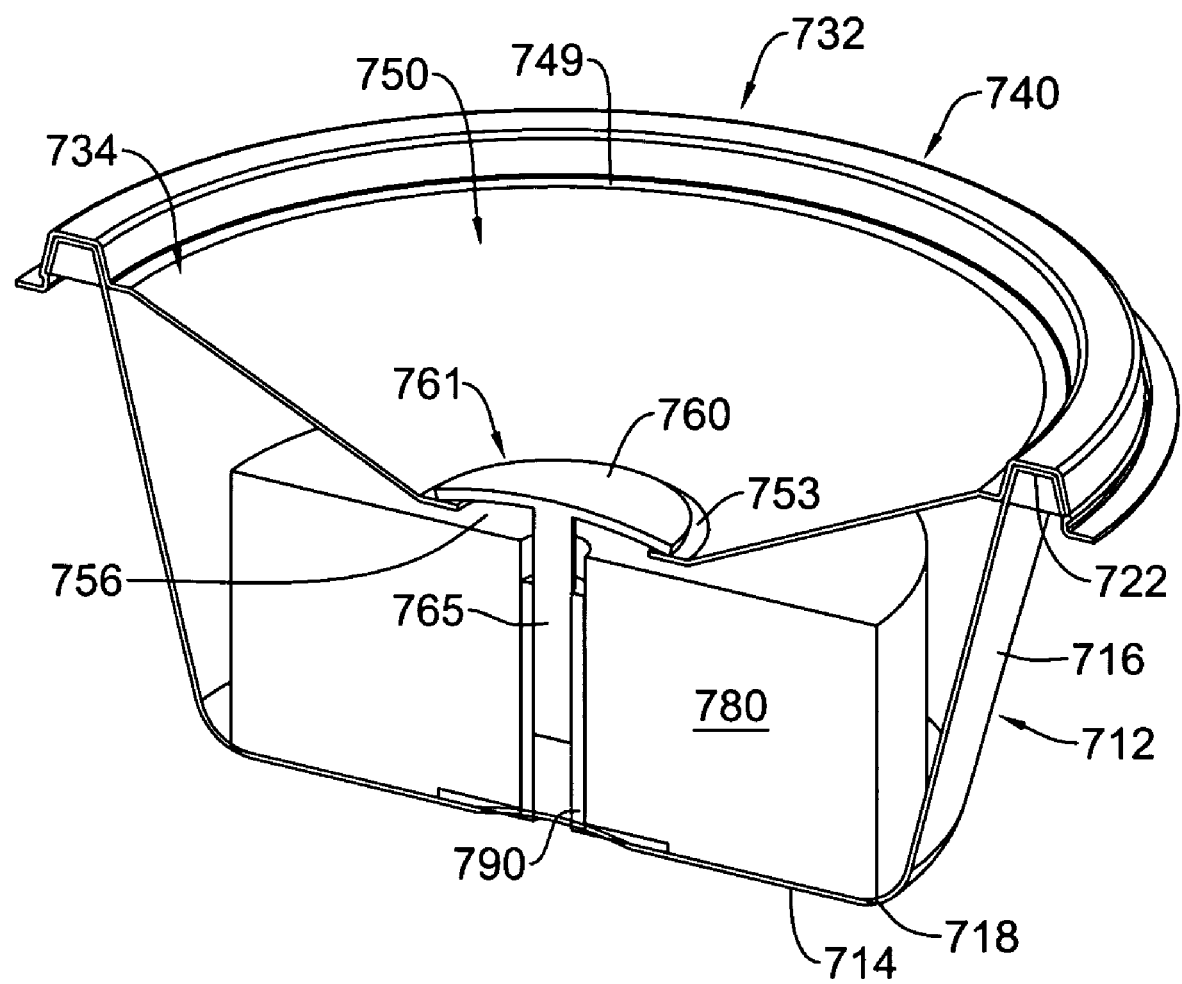

FIG. 9 and FIG. 10 are perspective cross-sectional views of another containment receptacle. In FIG. 9, there is provided a vessel 712 which includes a bottom 714, which can be any desired shape, but is substantially circular and planar in the depicted embodiment. The vessel 712 includes a wall 716 formed of unitary construction with and/or otherwise attached to the outer margin 718 of the bottom and upstanding therefrom to define an open top having an outer circumferential rim 722. In other embodiments, the vessel 712 can be square, rectangular, oval, polygonal, or any other shape, as desired. In the depicted embodiment, the wall 716 flares outwardly and upwardly from the bottom 714 so the circumference of the vessel at its open top is greater than its circumference adjacent the bottom 714. In other embodiments, the walls are not flared, or are flared inwardly. The vessel 712 may have many of the same size, shape, and/or other characteristics as the vessel 112 discussed in the above embodiments.

A lid 732 can be adapted to cover the open top vessel in sealing engagement with the rim 722. As in at least some of the embodiments discussed above, the lid 732 can include a rim portion 740 and a body portion 734. The body portion 734 may include a planar portion 749 and a recess portion 750. The recess portion 750 can be a majority of the lid 740 relative to the planar portion 749. The recess portion 750 can extend into the open top vessel 712. In some embodiments, the recess portion 750 extends from the planar portion 749 generally inwardly and downwardly toward the opening 756. As discussed above, some embodiments may not include the planar portion 749, in which case the recess portion 750 may extend directly from the rim portion 740. The recess portion 750 may have many of the same size, shape, and/or other characteristics as the recess portion 150 discussed in the above embodiments. As such, the recess portion 750 may be configured to change a contact angle of a stream of liquid hitting the recess portion 750, and/or direct at least a majority of the stream of liquid into the open top vessel through an opening 756 in the recess portion 750. The opening 756 may be surrounded by a region 753 having a different angle than the recess portion 750. For example, the portion 753 may be generally planar. Alternatively, the opening 756 can be surrounded by a region 753 having a surface forming an angle that can be greater or less than the angle forming the recess 750.

A plunger 761 can be disposed within the opening 756. The plunger 761 can be configured to move between an upper open position (FIG. 9) and a lower closed position (FIG. 10). The plunger 761 is configured to selectively seal the opening 756 in the closed position. The plunger 761 includes a head portion 760 connected to a stem portion 765. The stem portion 765 can be disposed within the opening 756. The stem portion 765 can be fixed to the head portion 760 in an orthogonal manner and extend away from the head portion 760. The stem portion 765 can be received in a sleeve element 790. The sleeve element 790 can be fixed to the vessel bottom 714 and extend away from the bottom 714. The sleeve element 790 can be configured to receive the stem portion 765 in slidable engagement. The plunger 761 can be manually moved between an open and closed position, as desired. In some embodiments, the plunger 761 can lock into place at the closed position.

In some or any of the embodiments discussed above, the interior of the vessel 112 or 712 may be provided with absorptive material, for example 780 in FIGS. 9 and 10. The absorptive material may help to absorb and maintain liquid admitted to the vessel. Many of a broad variety of absorbent material may be used, for example cotton, hydro gel material, cellulose fibrous material, or the like, or a broad variety of others. This absorptive material 780 is only shown in FIG. 9 and FIG. 10 however, absorptive material can be utilized in all embodiments, if desired.

Any of a wide variety of suitable material may be used to construct the vessel and/or the lid of any of the embodiments. For example, many suitable polymers, metals, glass, composites, of the like may be used. Some examples of suitable polymer materials may include various polypropylene, polyethylene, polyethylene glycol, polypropylene glycol, polyvinyl chloride, polyethylene terephthalate, PETG, polycarbonate, polystyrene, ABS, nylon, fluoropolymers, vinyls, styrenics, polyesters, or other such polymers, or the like. Suitable metals may include stainless steel, aluminum, tin, or the like, or other.

In some embodiments, it is also contemplated that anti-microbial, disinfectant, sanitizing, or other such agents may be incorporated into the material of the vessel and/or the lid and/or absorbent material. For example, such agents may be added to or incorporated into the polymer, or other material, that is then used to form the lid and/or vessel. Likewise, such agents could be added to or otherwise incorporated into the absorbent material. In some embodiments, the anti-microbial, disinfectant, sanitizing, or other such agents could simply be added to the bottom of the vessel prior to or after introducing liquid medical waste into the vessel. Such agents may aid in reducing and/or eliminating certain infectious agents that may be present in the liquid medical waste.

Any of a wide variety of suitable manufacturing processes may also be used to create the lid and/or vessel of any of the embodiments. For example, processes such as vacuum forming, molding, casting, die cutting, welding, soldering, adhesive bonding, material bending or forming, of the like may be used to construct the vessel and/or the lid of any of the embodiments. In some embodiments, for example, the vessel and lid can formed by vacuum forming a suitable polymer into the desired shape. The vessel walls and the portions of the lid may be formed to any suitable thickness for its intended use. It may be desired to provide the vessel and/or lid with desired rigidity and flexibility characteristics. For example, it may be desirable that the lid and/or vessel be somewhat shock resistant such that it is resistant to shattering or otherwise breaking if dropped. Additionally, as discussed above, it may be desirable to provide at least portions of the lid, for example the recessed portion, with sufficient flexibility characteristics to aid in directing fluid into the vessel. In some embodiments, it may be desirable for the lid and/or vessel, or portions thereof, to be made using a clear polymer or other material to permit the visual observation of the contents of the vessel by medical personnel. In another embodiment, the vessel and/or lid can be colored red in accordance with conventional labeling for receptacles of hazardous waste material.

The present invention should not be considered limited to the particular examples described above, but rather should be understood to cover all aspects of the invention as fairly set out in the attached claims. Various modifications, equivalent processes, as well as numerous structures to which the present invention can be applicable will be readily apparent to those of skill in the art to which the present invention is directed upon review of the instant specification.

What is claimed is:

1. A liquid medical waste receptacle comprising:
    an open top vessel having a bottom and an upstanding wall defining an upper rim; and
    a lid adapted to cover the open top vessel in engagement with the upper rim, the lid comprising a rim and a body portion, the body portion defining a recess portion, the recess portion having at least 40 fingers adapted to extend into the open top vessel, wherein at least selected fingers have a proximal section, a distal section, that extends into the open top vessel, and an intermediate section disposed between the proximal and distal sections, the proximal section being closer to the rim than the distal section, wherein the proximal section or the intermediate section includes a flexibility that is greater than the flexibility of at least a portion of the distal section, and wherein the intermediate section or proximal section of the selected fingers has a width that is less than the width of the distal section of the selected fingers, such that the proximal section or the intermediate section absorbs the energy from the liquid medical waste hitting the recess portion and redirects at least a majority of the liquid into the open top vessel.

2. A liquid medical waste receptacle comprising:
    an open top vessel having a bottom and an upstanding wall defining an upper rim; and
    a lid adapted to cover the open top vessel in engagement with the upper rim, the lid comprising a rim and a body portion, the body portion defining a recess portion, the recess portion having a plurality of fingers adapted to extend into the open top vessel, wherein at least selected fingers have a proximal section, a distal section, and an intermediate section disposed between the proximal and distal sections, wherein the proximal section or the intermediate section includes a flexibility that is greater than the flexibility of at least a portion of the distal section, such that the proximal section or the intermediate section absorbs the energy from the liquid medical waste hitting the recess portion and redirects at least a majority of the liquid into the open top vessel, wherein the intermediate section includes a flexibility that is greater than the flexibility of at least a portion of the proximal section.

3. The liquid medical waste receptacle according to claim 2, wherein the recess portion comprises a majority of the body portion.

4. The liquid medical waste receptacle according to claim 2, wherein the proximal section includes a flexibility that is greater than the flexibility of at least a portion of the intermediate section.

5. The liquid medical waste receptacle according to claim 2, wherein the recess portion is formed by at least 10 fingers.

6. The liquid medical waste receptacle according to claim 2, wherein the recess portion is formed by at least 20 fingers.

7. The liquid medical waste receptacle according to claim 2, wherein the recess portion is formed by at least 30 fingers.

8. The liquid medical waste receptacle according to claim 2, wherein the recess portion is formed by at least 40 fingers.

9. The liquid medical waste receptacle according to claim 2, wherein the recess portion is formed by at least 50 fingers.

10. The liquid medical waste receptacle according to claim 2, wherein at least selected plurality of fingers have a width defined by a first side and a second side and at least a portion of the first side and second side are parallel.

11. The liquid medical waste receptacle according to claim 2, wherein at least selected plurality of fingers have a width defined by a first side and a second side and at least a portion of the first side and second side are non-parallel.

12. The liquid medical waste receptacle according to claim 2, wherein the body portion further includes a planar portion disposed between the rim and the recess portion, the fingers of the recess portion extending from the planar portion into the open top vessel.

13. The liquid medical waste receptacle according to claim 2, wherein the fingers of the recess portion extending from the rim into the open top vessel.

14. A liquid medical waste receptacle comprising:
    an open top vessel having a bottom and an upstanding wall defining an upper rim; and
    a lid adapted to cover the open top vessel in sealing engagement with the upper rim, the lid comprising a rim and a body portion, the body portion comprises a sloping portion that extends slopingly and downwardly into the open top vessel, wherein a plurality of apertures located on the sloping portion form at least one annular pattern, wherein at least selected plurality of annular apertures include an overhang extending from and over selected annular apertures.

* * * * *